US010278627B2

(12) United States Patent
Schroeter et al.

(10) Patent No.: US 10,278,627 B2
(45) Date of Patent: *May 7, 2019

(54) SYSTEM AND METHOD FOR PERFORMING A DIAGNOSTIC ANALYSIS OF PHYSIOLOGICAL INFORMATION

(71) Applicant: AT&T INTELLECTUAL PROPERTY I, LP, Atlanta, GA (US)

(72) Inventors: Horst Juergen Schroeter, Vero Beach, FL (US); E-Lee Chang, Mableton, GA (US); Linda Roberts, Boynton Beach, FL (US); Madhur Khandelwal, Atlanta, GA (US); Darnell Clayton, Atlanta, GA (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 89 days.

This patent is subject to a terminal disclaimer.

(21) Appl. No.: 15/195,280

(22) Filed: Jun. 28, 2016

(65) Prior Publication Data

US 2016/0306939 A1 Oct. 20, 2016

Related U.S. Application Data

(63) Continuation of application No. 12/271,600, filed on Nov. 14, 2008, now Pat. No. 9,408,537.

(51) Int. Cl.
*A61B 5/1455* (2006.01)
*G06F 19/00* (2018.01)
(Continued)

(52) U.S. Cl.
CPC ........ *A61B 5/14551* (2013.01); *A61B 5/0022* (2013.01); *A61B 5/01* (2013.01);
(Continued)

(58) Field of Classification Search
None
See application file for complete search history.

(56) References Cited

U.S. PATENT DOCUMENTS

| | | | |
|---|---|---|---|
| 5,437,278 A * | 8/1995 | Wilk .................... | A61B 5/4839 600/300 |
| 5,660,176 A * | 8/1997 | Iliff ....................... | G06F 19/322 600/300 |

(Continued)

*Primary Examiner* — Carl H Layno
*Assistant Examiner* — Qingjun Kong
(74) *Attorney, Agent, or Firm* — Guntin & Gust, PLC; Douglas Schnabel

(57) ABSTRACT

A system that incorporates teachings of the present disclosure may include, for example, an avatar engine having a controller to retrieve a user profile of a user, present the user an avatar having characteristics that correlate to the user profile, detect one or more responses of the user during a communication exchange between the user and the avatar, identify from the one or more responses a need to determine a medical status of the user, establish communications with a medical diagnostic system, receive physiological information associated with the user, submit the physiological information to the medical diagnostic system, receive from the medical diagnostic system a diagnostic analysis of the physiological information, and present the diagnostic analysis to at least one of the user and a medical agent of the user, wherein the user is presented the diagnostic analysis by way of the avatar. Other embodiments are disclosed.

20 Claims, 9 Drawing Sheets

(51) Int. Cl.
  *G16H 50/20* (2018.01)
  *G16H 10/60* (2018.01)
  *G16H 40/63* (2018.01)
  *G16H 10/20* (2018.01)
  *A61B 5/00* (2006.01)
  *A61B 5/01* (2006.01)
  *A61B 5/024* (2006.01)
  *A61B 5/145* (2006.01)
  *A61B 5/021* (2006.01)
  *G06N 3/00* (2006.01)

(52) U.S. Cl.
  CPC .......... *A61B 5/021* (2013.01); *A61B 5/02416* (2013.01); *A61B 5/14532* (2013.01); *A61B 5/4842* (2013.01); *A61B 5/4872* (2013.01); *A61B 5/7246* (2013.01); *A61B 5/744* (2013.01); *A61B 5/7465* (2013.01); *G06F 19/00* (2013.01); *G06F 19/3418* (2013.01); *G06F 19/36* (2013.01); *G06N 3/006* (2013.01); *G16H 10/20* (2018.01); *G16H 10/60* (2018.01); *G16H 40/63* (2018.01); *G16H 50/20* (2018.01)

(56) References Cited

U.S. PATENT DOCUMENTS

| | | | |
|---|---|---|---|
| 6,190,313 B1 | 2/2001 | Hinkle | |
| 6,425,764 B1* | 7/2002 | Lamson | A61M 21/00 434/236 |
| 6,641,532 B2* | 11/2003 | Iliff | G06F 19/322 600/300 |
| 8,469,713 B2* | 6/2013 | Kron | G09B 23/28 434/156 |
| 2002/0065682 A1* | 5/2002 | Goldenberg | G06F 19/324 705/2 |
| 2002/0107824 A1* | 8/2002 | Ahmed | G06F 19/345 706/46 |
| 2004/0002634 A1* | 1/2004 | Nihtila | A61B 5/0002 600/300 |
| 2004/0121295 A1* | 6/2004 | Stuart | G09B 23/28 434/262 |
| 2005/0015115 A1* | 1/2005 | Sullivan | A61B 5/0002 607/5 |
| 2005/0273509 A1* | 12/2005 | Brown | A61B 5/0002 709/224 |
| 2006/0100018 A1* | 5/2006 | Ganz | G06Q 30/02 463/42 |
| 2007/0021979 A1* | 1/2007 | Cosentino | A61B 5/0031 705/2 |
| 2007/0050715 A1* | 3/2007 | Behar | A61B 5/0002 715/706 |
| 2007/0129610 A1* | 6/2007 | Squilla | G06F 19/3418 600/300 |
| 2007/0166690 A1* | 7/2007 | Johnson | G09B 5/14 434/365 |
| 2007/0167204 A1* | 7/2007 | Lyle | A63F 13/12 463/9 |
| 2008/0052116 A1* | 2/2008 | Iliff | G06F 19/322 705/2 |
| 2008/0146334 A1* | 6/2008 | Kil | G06F 19/345 463/36 |
| 2008/0274755 A1* | 11/2008 | Cholkar | H04W 8/18 455/461 |
| 2008/0303811 A1* | 12/2008 | Van Luchene | A63F 13/12 345/419 |
| 2009/0037470 A1* | 2/2009 | Schmidt | G16H 10/60 |
| 2009/0044113 A1* | 2/2009 | Jones | G06T 13/40 715/707 |
| 2009/0112538 A1* | 4/2009 | Anderson | G06Q 10/06 703/6 |
| 2009/0164917 A1* | 6/2009 | Kelly | G06F 3/011 715/757 |
| 2009/0254417 A1* | 10/2009 | Beilby | G06N 3/004 706/45 |
| 2009/0293079 A1* | 11/2009 | McKee | G06Q 10/105 725/10 |
| 2009/0325701 A1* | 12/2009 | Andres Del Valle | A63F 13/12 463/36 |
| 2010/0046806 A1* | 2/2010 | Baughman | G06F 21/316 382/115 |
| 2010/0070987 A1* | 3/2010 | Amento | H04H 60/33 725/10 |
| 2010/0121156 A1* | 5/2010 | Yoo | G06F 19/3418 600/300 |

* cited by examiner

200

600

SYSTEM AND METHOD FOR PERFORMING A DIAGNOSTIC ANALYSIS OF PHYSIOLOGICAL INFORMATION

RELATED MATTERS

This application is a Continuation and claims priority to U.S. patent application Ser. No. 12/271,600 filed on Nov. 14, 2008, now U.S. Pat. No. 9,408,537. The contents of the foregoing application are hereby incorporated by reference into this application as if set forth herein in full.

FIELD OF THE DISCLOSURE

The present disclosure relates generally to diagnostic techniques and more specifically to a system and method for performing a diagnostic analysis of physiological information.

BACKGROUND

It is common place for individuals to schedule an appointment with a doctor to request a general checkup or to diagnose an ailment. A physician can perform diagnostics analysis of physiological information of a patient such as blood pressure, temperature, or a blood sample to determine the health of the patient and to diagnose ailments.

Machines such as blood pressure sensors, temperature sensors, heart rate sensors, glucose sensors, and so on, can be used outside of a doctor's office. Some individuals can share measurements from these machines with an on-line system as an alternative means of self diagnoses.

DETAILED DESCRIPTION

One embodiment of the present disclosure can entail an avatar engine having a controller to retrieve a user profile of a user, present the user an avatar having characteristics that correlate to the user profile, detect one or more responses of the user during a communication exchange between the user and the avatar, identify from the one or more responses a need to determine a medical status of the user, establish communications with a medical diagnostic system, receive physiological information associated with the user, submit the physiological information to the medical diagnostic system, receive from the medical diagnostic system a diagnostic analysis of the physiological information, and present the diagnostic analysis to at least one of the user and a medical agent of the user, wherein the user is presented the diagnostic analysis by way of the avatar.

Another embodiment of the present disclosure can entail presenting a user an avatar having characteristics that correlate to a profile of the user, identifying from a communication exchange between the user and the avatar a need to physiologically analyze the user, receiving physiological information associated with the user, submitting the physiological information to a medical system, receiving from the medical system a diagnostic analysis of the physiological information, and presenting the diagnostic analysis by way of the avatar.

Yet another embodiment of the present disclosure can entail a computer-readable storage medium having computer instructions for conducting a communication exchange between a user and an avatar, submitting to a medical system physiological information associated with the user, receiving from the medical system a diagnostic analysis of the physiological information, and presenting the diagnostic analysis by way of the avatar.

Another embodiment of the present disclosure can delivering an interactive avatar service that performs physiological diagnostic services.

Yet another embodiment of the present disclosure can entail a system having a controller to provide diagnostic analysis of physiological information supplied by an interactive avatar system.

Figure 1:
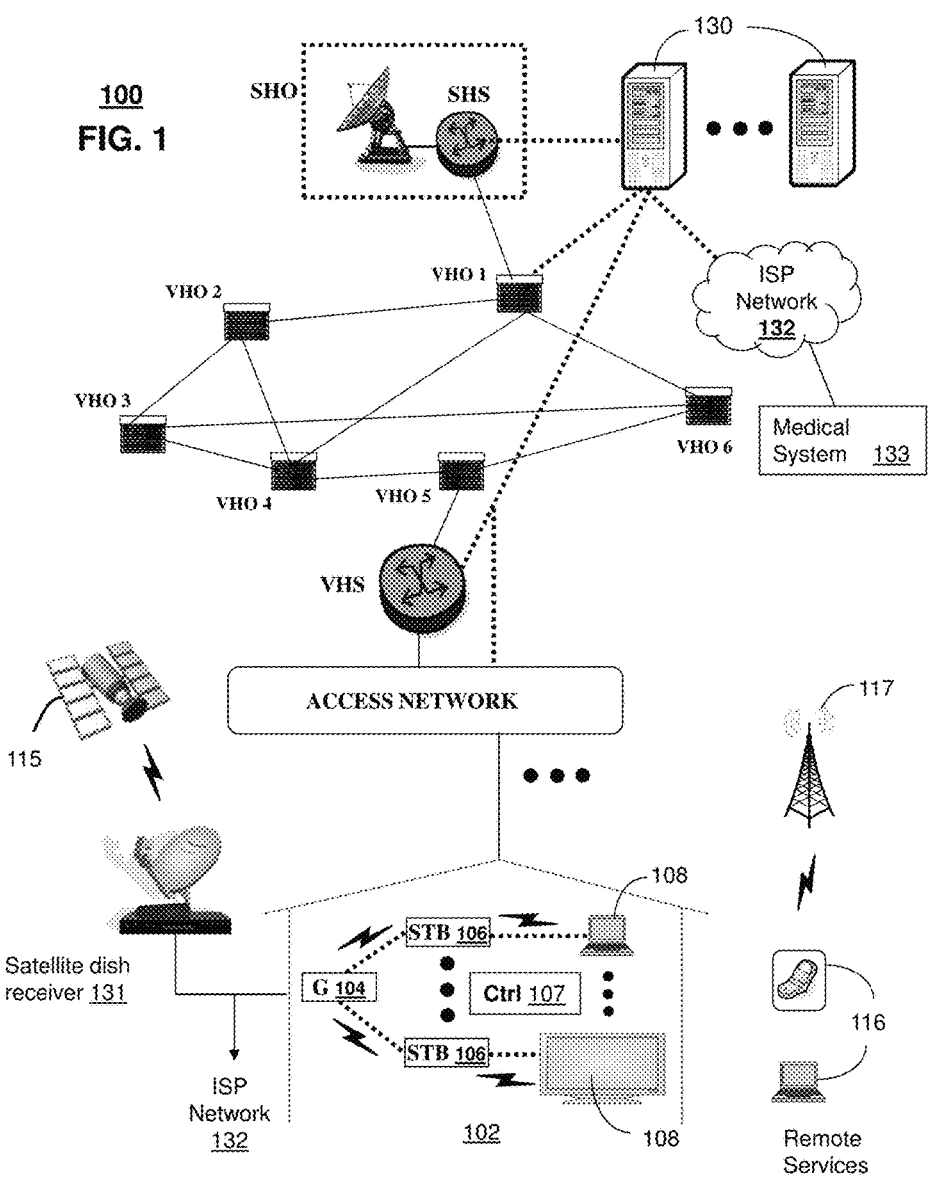
FIGS. 1-4 depict illustrative embodiments of communication systems that provide media services.

FIG. 1 depicts an illustrative embodiment of a first communication system 100 for delivering media content. The communication system 100 can represent an Internet Protocol Television (IPTV) broadcast media system. In a typical IPTV infrastructure, there is a super head-end office (SHO) with at least one super headend office server (SHS) which receives national media programs from satellite and/or media servers from service providers of multimedia broadcast channels. In the present context, media programs can represent audio content, moving image content such as videos, still image content, and/or combinations thereof. The SHS server forwards IP packets associated with the media content to video head-end servers (VHS) via a network of aggregation points such as video head-end offices (VHO) according to a common multicast communication method.

The VHS then distributes multimedia broadcast programs via an access network to commercial and/or residential buildings 102 housing a gateway 104 (such as a residential gateway or RG). The access network can represent a bank of digital subscriber line access multiplexers (DSLAMs) located in a central office or a service area interface that provide broadband services over optical links or copper twisted pairs to buildings 102. The gateway 104 distributes broadcast signals to media processors 106 such as Set-Top Boxes (STBs) which in turn present broadcast selections to media devices 108 such as computers or television sets managed in some instances by a media controller 107 (such as an infrared or RF remote control). Unicast traffic can also be exchanged between the media processors 106 and subsystems of the IPTV media system for services such as video-on-demand (VoD). It will be appreciated by one of ordinary skill in the art that the media devices 108 and/or portable communication devices 116 shown in FIG. 1 can be an integral part of the media processor 106 and can be communicatively coupled to the gateway 104. In this particular embodiment, an integral device such as described can receive, respond, process and present multicast or unicast media content.

The IPTV media system can be coupled to one or more computing devices 130 a portion of which can operate as a web server for providing portal services over an Internet Service Provider (ISP) network 132 to fixed line media devices 108 or portable communication devices 116 by way of a wireless access point 117 providing Wireless Fidelity or WiFi services, or cellular communication services (such as GSM, CDMA, UMTS, WiMAX, etc.).

Another distinct portion of the one or more computing devices 130 can be used as an avatar engine (herein referred to as avatar engine 130) for generating and managing interactive avatars which users of the first communication system 100 can be presented for general assistance and presentation of interactive television (iTV) services as well as other services such as described below in FIG. 7. The avatar engine 130 can use common imaging technology for creating avatars with human-like or animated qualities. The avatar engine 130 can also use common speech recognition and speech synthesis technology to produce an interactive avatar. With these technologies, the avatar engine 130 can determine the user's needs from a communication exchange between the user and the avatar image produced by the avatar engine.

The avatar engine 130 can be coupled by way of the ISP network 132 to a medical system 133 that employs common communication and computing technologies. The medical system 133 can have a database of diagnostic information which can be accessed by an artificial intelligence system operating in the medical system to analyze physiological information such as blood pressure, heart rate, glucose levels, weight, body fat, and so on, supplied by a user of the avatar by way of the avatar engine 130. The artificial intelligence algorithms operating in the medical system 133 can emulate common diagnostic analysis techniques employed by physicians to detect patient ailments and to provide mitigation recommendations in some instances with a prognosis. The medical system 133 can also provide recommendations to improve the avatar user's health.

A satellite broadcast television system can be used in place of the IPTV media system. In this embodiment, signals transmitted by a satellite 115 can be intercepted by a satellite dish receiver 131 coupled to building 102 which conveys media signals to the media processors 106. The media receivers 106 can be equipped with a broadband port to the ISP network 132. Although not shown, the communication system 100 can also be combined or replaced with analog or digital broadcast distributions systems such as cable TV systems.

Figure 2:
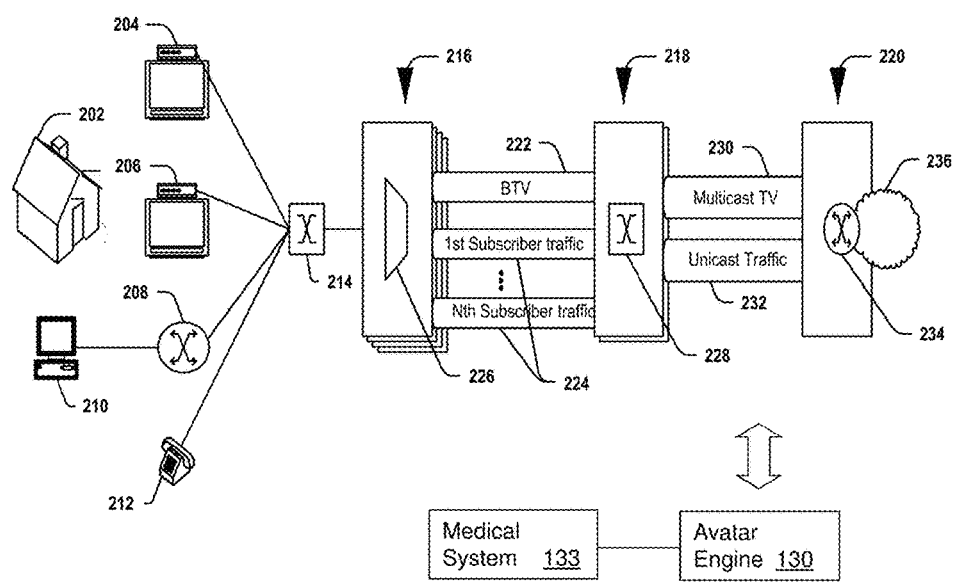

FIG. 2 depicts an illustrative embodiment of a second communication system 200 for delivering media content. Communication system 200 can be overlaid or operably coupled with communication system 100 as another representative embodiment of said communication system. The system 200 includes a distribution switch/router system 228 at a central office 218. The distribution switch/router system 228 receives video data via a multicast television stream 230 from a second distribution switch/router 234 at an intermediate office 220. The multicast television stream 230 includes Internet Protocol (IP) data packets addressed to a multicast IP address associated with a television channel. The distribution switch/router system 228 can cache data associated with each television channel received from the intermediate office 220.

The distribution switch/router system 228 also receives unicast data traffic from the intermediate office 220 via a unicast traffic stream 232. The unicast traffic stream 232 includes data packets related to devices located at a particular residence, such as the residence 202. For example, the unicast traffic stream 232 can include data traffic related to a digital subscriber line, a telephone line, another data connection, or any combination thereof. To illustrate, the unicast traffic stream 232 can communicate data packets to and from a telephone 212 associated with a subscriber at the residence 202. The telephone 212 can be a Voice over Internet Protocol (VoIP) telephone. To further illustrate, the unicast traffic stream 232 can communicate data packets to and from a personal computer 210 at the residence 202 via one or more data routers 208. In an additional illustration, the unicast traffic stream 232 can communicate data packets to and from a set-top box device, such as the set-top box devices 204, 206. The unicast traffic stream 232 can communicate data packets to and from the devices located at the residence 202 via one or more residential gateways 214 associated with the residence 202.

The distribution switch/router system 228 can send data to one or more access switch/router systems 226. The access switch/router system 226 can include or be included within a service area interface 216. In a particular embodiment, the access switch/router system 226 can include a DSLAM. The access switch/router system 226 can receive data from the distribution switch/router system 228 via a broadcast television (BTV) stream 222 and a plurality of unicast subscriber traffic streams 224. The BTV stream 222 can be used to communicate video data packets associated with a multicast stream.

For example, the BTV stream 222 can include a multicast virtual local area network (VLAN) connection between the distribution switch/router system 228 and the access switch/router system 226. Each of the plurality of subscriber traffic streams 224 can be used to communicate subscriber specific data packets. For example, the first subscriber traffic stream can communicate data related to a first subscriber, and the nth subscriber traffic stream can communicate data related to an nth subscriber. Each subscriber to the system 200 can be associated with a respective subscriber traffic stream 224. The subscriber traffic stream 224 can include a subscriber VLAN connection between the distribution switch/router system 228 and the access switch/router system 226 that is associated with a particular set-top box device 204, 206, a particular residence 202, a particular residential gateway 214, another device associated with a subscriber, or any combination thereof.

In an illustrative embodiment, a set-top box device, such as the set-top box device 204, receives a channel change command from an input device, such as a remoter control device. The channel change command can indicate selection of an IPTV channel. After receiving the channel change command, the set-top box device 204 generates channel selection data that indicates the selection of the IPTV channel. The set-top box device 204 can send the channel selection data to the access switch/router system 226 via the residential gateway 214. The channel selection data can include an Internet Group Management Protocol (IGMP) Join request. In an illustrative embodiment, the access switch/router system 226 can identify whether it is joined to a multicast group associated with the requested channel based on information in the IGMP Join request.

If the access switch/router system 226 is not joined to the multicast group associated with the requested channel, the access switch/router system 226 can generate a multicast stream request. The multicast stream request can be generated by modifying the received channel selection data. In an illustrative embodiment, the access switch/router system 226 can modify an IGMP Join request to produce a proxy IGMP Join request. The access switch/router system 226 can send the multicast stream request to the distribution switch/router system 228 via the BTV stream 222. In response to receiving the multicast stream request, the distribution switch/router system 228 can send a stream associated with the requested channel to the access switch/router system 226 via the BTV stream 222.

The avatar engine 130 of FIG. 1 can be operably coupled to the second communication system 200 for purposes similar to those described above.

Figure 3:
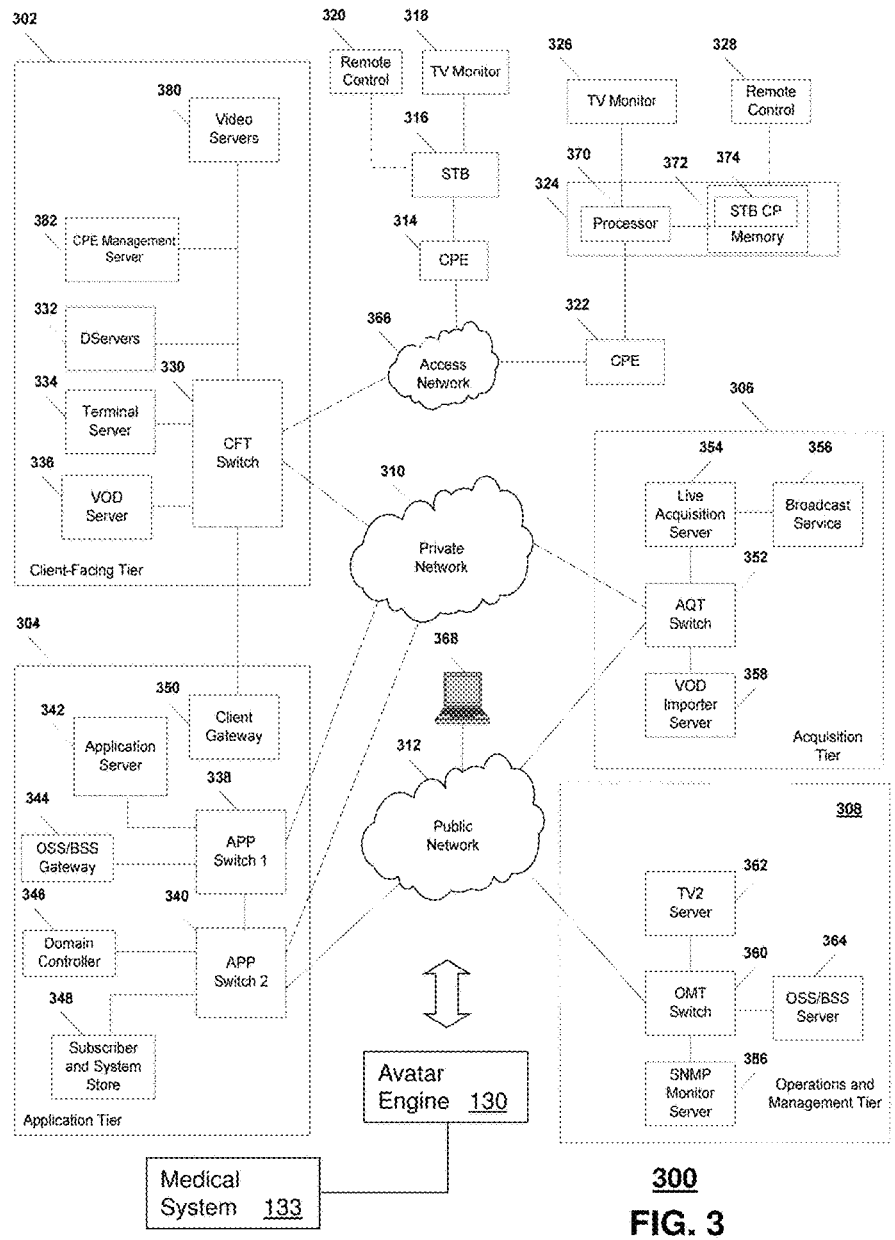

FIG. 3 depicts an illustrative embodiment of a third communication system 300 for delivering media content. Communication system 300 can be overlaid or operably coupled with communication systems 100-200 as another representative embodiment of said communication systems. As shown, the system 300 can include a client facing tier 302, an application tier 304, an acquisition tier 306, and an operations and management tier 308. Each tier 302, 304, 306, 308 is coupled to a private network 310, such as a network of common packet-switched routers and/or switches; to a public network 312, such as the Internet; or to both the private network 310 and the public network 312. For example, the client-facing tier 302 can be coupled to the private network 310. Further, the application tier 304 can be coupled to the private network 310 and to the public network 312. The acquisition tier 306 can also be coupled to the private network 310 and to the public network 312. Additionally, the operations and management tier 308 can be coupled to the public network 312.

As illustrated in FIG. 3, the various tiers 302, 304, 306, 308 communicate with each other via the private network 310 and the public network 312. For instance, the client-facing tier 302 can communicate with the application tier 304 and the acquisition tier 306 via the private network 310. The application tier 304 can communicate with the acquisition tier 306 via the private network 310. Further, the application tier 304 can communicate with the acquisition tier 306 and the operations and management tier 308 via the public network 312. Moreover, the acquisition tier 306 can communicate with the operations and management tier 308 via the public network 312. In a particular embodiment, elements of the application tier 304, including, but not limited to, a client gateway 350, can communicate directly with the client-facing tier 302.

The client-facing tier 302 can communicate with user equipment via an access network 366, such as an IPTV access network. In an illustrative embodiment, customer premises equipment (CPE) 314, 322 can be coupled to a local switch, router, or other device of the access network 366. The client-facing tier 302 can communicate with a first representative set-top box device 316 via the first CPE 314 and with a second representative set-top box device 324 via the second CPE 322. In a particular embodiment, the first representative set-top box device 316 and the first CPE 314 can be located at a first customer premise, and the second representative set-top box device 324 and the second CPE 322 can be located at a second customer premise.

In another particular embodiment, the first representative set-top box device 316 and the second representative set-top box device 324 can be located at a single customer premise, both coupled to one of the CPE 314, 322. The CPE 314, 322 can include routers, local area network devices, modems, such as digital subscriber line (DSL) modems, any other suitable devices for facilitating communication between a set-top box device and the access network 366, or any combination thereof.

In an illustrative embodiment, the client-facing tier 302 can be coupled to the CPE 314, 322 via fiber optic cables. In another illustrative embodiment, the CPE 314, 322 can include DSL modems that are coupled to one or more network nodes via twisted pairs, and the client-facing tier 302 can be coupled to the network nodes via fiber-optic cables. Each set-top box device 316, 324 can process data received via the access network 366, via a common IPTV software platform.

The first set-top box device 316 can be coupled to a first external display device, such as a first television monitor 318, and the second set-top box device 324 can be coupled to a second external display device, such as a second television monitor 326. Moreover, the first set-top box device 316 can communicate with a first remote control 320, and the second set-top box device 324 can communicate with a second remote control 328. The set-top box devices 316, 324 can include IPTV set-top box devices; video gaming devices or consoles that are adapted to receive IPTV content; personal computers or other computing devices that are adapted to emulate set-top box device functionalities; any other device adapted to receive IPTV content and transmit data to an IPTV system via an access network; or any combination thereof.

In an illustrative, non-limiting embodiment, each set-top box device 316, 324 can receive data, video, or any combination thereof, from the client-facing tier 302 via the access network 366 and render or display the data, video, or any combination thereof, at the display device 318, 326 to which it is coupled. In an illustrative embodiment, the set-top box devices 316, 324 can include tuners that receive and decode television programming signals or packet streams for transmission to the display devices 318, 326. Further, the set-top box devices 316, 324 can each include a STB processor 370 and a STB memory device 372 that is accessible to the STB processor 370. In one embodiment, a computer program, such as the STB computer program 374, can be embedded within the STB memory device 372.

In an illustrative embodiment, the client-facing tier 302 can include a client-facing tier (CFT) switch 330 that manages communication between the client-facing tier 302 and the access network 366 and between the client-facing tier 302 and the private network 310. As illustrated, the CFT switch 330 is coupled to one or more distribution servers, such as Distribution-servers (D-servers) 332, that store, format, encode, replicate, or otherwise manipulate or prepare video content for communication from the client-facing tier 302 to the set-top box devices 316, 324. The CFT switch 330 can also be coupled to a terminal server 334 that provides terminal devices with a point of connection to the IPTV system 300 via the client-facing tier 302.

In a particular embodiment, the CFT switch 330 can be coupled to a VoD server 336 that stores or provides VoD content imported by the IPTV system 300. Further, the CFT switch 330 is coupled to one or more video servers 380 that receive video content and transmit the content to the set-top boxes 316, 324 via the access network 366. The client-facing tier 302 may include a CPE management server 382 that manages communications to and from the CPE 314 and the CPE 322. For example, the CPE management server 382 may collect performance data associated with the set-top box devices 316, 324 from the CPE 314 or the CPE 322 and forward the collected performance data to a server associated with the operations and management tier 308.

In an illustrative embodiment, the client-facing tier 302 can communicate with a large number of set-top boxes, such as the representative set-top boxes 316, 324, over a wide geographic area, such as a metropolitan area, a viewing area, a statewide area, a regional area, a nationwide area or any other suitable geographic area, market area, or subscriber or customer group that can be supported by networking the client-facing tier 302 to numerous set-top box devices. In a particular embodiment, the CFT switch 330, or any portion thereof, can include a multicast router or switch that communicates with multiple set-top box devices via a multicast-enabled network.

As illustrated in FIG. 3, the application tier 304 can communicate with both the private network 310 and the public network 312. The application tier 304 can include a first application tier (APP) switch 338 and a second APP switch 340. In a particular embodiment, the first APP switch 338 can be coupled to the second APP switch 340. The first APP switch 338 can be coupled to an application server 342 and to an OSS/BSS gateway 344. In a particular embodiment, the application server 342 can provide applications to the set-top box devices 316, 324 via the access network 366, which enable the set-top box devices 316, 324 to provide functions, such as interactive program guides, video gaming, display, messaging, processing of VoD material and other IPTV content, etc. In an illustrative embodiment, the application server 342 can provide location information to the set-top box devices 316, 324. In a particular embodiment, the OSS/BSS gateway 344 includes operation systems and support (OSS) data, as well as billing systems and support (BSS) data. In one embodiment, the OSS/BSS gateway 344 can provide or restrict access to an OSS/BSS server 364 that stores operations and billing systems data.

The second APP switch 340 can be coupled to a domain controller 346 that provides Internet access, for example, to users at their computers 368 via the public network 312. For example, the domain controller 346 can provide remote Internet access to IPTV account information, e-mail, personalized Internet services, or other online services via the public network 312. In addition, the second APP switch 340 can be coupled to a subscriber and system store 348 that includes account information, such as account information that is associated with users who access the IPTV system 300 via the private network 310 or the public network 312. In an illustrative embodiment, the subscriber and system store 348 can store subscriber or customer data and create subscriber or customer profiles that are associated with IP addresses, stock-keeping unit (SKU) numbers, other identifiers, or any combination thereof, of corresponding set-top box devices 316, 324. In another illustrative embodiment, the subscriber and system store can store data associated with capabilities of set-top box devices associated with particular customers.

In a particular embodiment, the application tier 304 can include a client gateway 350 that communicates data directly to the client-facing tier 302. In this embodiment, the client gateway 350 can be coupled directly to the CFT switch 330. The client gateway 350 can provide user access to the private network 310 and the tiers coupled thereto. In an illustrative embodiment, the set-top box devices 316, 324 can access the IPTV system 300 via the access network 366, using information received from the client gateway 350. User devices can access the client gateway 350 via the access network 366, and the client gateway 350 can allow such devices to access the private network 310 once the devices are authenticated or verified. Similarly, the client gateway 350 can prevent unauthorized devices, such as hacker computers or stolen set-top box devices from accessing the private network 310, by denying access to these devices beyond the access network 366.

For example, when the first representative set-top box device 316 accesses the client-facing tier 302 via the access network 366, the client gateway 350 can verify subscriber information by communicating with the subscriber and system store 348 via the private network 310. Further, the client gateway 350 can verify billing information and status by communicating with the OSS/BSS gateway 344 via the private network 310. In one embodiment, the OSS/BSS gateway 344 can transmit a query via the public network 312 to the OSS/BSS server 364. After the client gateway 350 confirms subscriber and/or billing information, the client gateway 350 can allow the set-top box device 316 to access IPTV content and VoD content at the client-facing tier 302. If the client gateway 350 cannot verify subscriber information for the set-top box device 316, because it is connected to an unauthorized twisted pair, the client gateway 350 can block transmissions to and from the set-top box device 316 beyond the access network 366.

As indicated in FIG. 3, the acquisition tier 306 includes an acquisition tier (AQT) switch 352 that communicates with the private network 310. The AQT switch 352 can also communicate with the operations and management tier 308 via the public network 312. In a particular embodiment, the AQT switch 352 can be coupled to one or more live Acquisition-servers (A-servers) 354 that receive or acquire television content, movie content, advertisement content, other video content, or any combination thereof, from a broadcast service 356, such as a satellite acquisition system or satellite head-end office. In a particular embodiment, the live acquisition server 354 can transmit content to the AQT switch 352, and the AQT switch 352 can transmit the content to the CFT switch 330 via the private network 310.

In an illustrative embodiment, content can be transmitted to the D-servers 332, where it can be encoded, formatted, stored, replicated, or otherwise manipulated and prepared for communication from the video server(s) 380 to the set-top box devices 316, 324. The CFT switch 330 can receive content from the video server(s) 380 and communicate the content to the CPE 314, 322 via the access network 366. The set-top box devices 316, 324 can receive the content via the CPE 314, 322, and can transmit the content to the television monitors 318, 326. In an illustrative embodiment, video or audio portions of the content can be streamed to the set-top box devices 316, 324.

Further, the AQT switch 352 can be coupled to a video-on-demand importer server 358 that receives and stores television or movie content received at the acquisition tier 306 and communicates the stored content to the VoD server 336 at the client-facing tier 302 via the private network 310. Additionally, at the acquisition tier 306, the VoD importer server 358 can receive content from one or more VoD sources outside the IPTV system 300, such as movie studios and programmers of non-live content. The VoD importer server 358 can transmit the VoD content to the AQT switch 352, and the AQT switch 352, in turn, can communicate the material to the CFT switch 330 via the private network 310. The VoD content can be stored at one or more servers, such as the VoD server 336.

When users issue requests for VoD content via the set-top box devices 316, 324, the requests can be transmitted over the access network 366 to the VoD server 336, via the CFT switch 330. Upon receiving such requests, the VoD server 336 can retrieve the requested VoD content and transmit the content to the set-top box devices 316, 324 across the access network 366, via the CFT switch 330. The set-top box devices 316, 324 can transmit the VoD content to the television monitors 318, 326. In an illustrative embodiment, video or audio portions of VoD content can be streamed to the set-top box devices 316, 324.

FIG. 3 further illustrates that the operations and management tier 308 can include an operations and management tier (OMT) switch 360 that conducts communication between the operations and management tier 308 and the public network 312. In the embodiment illustrated by FIG. 3, the OMT switch 360 is coupled to a TV2 server 362. Additionally, the OMT switch 360 can be coupled to an OSS/BSS server 364 and to a simple network management protocol monitor 386 that monitors network devices within or coupled to the IPTV system 300. In a particular embodiment, the OMT switch 360 can communicate with the AQT switch 352 via the public network 312.

The OSS/BSS server 364 may include a cluster of servers, such as one or more CPE data collection servers that are adapted to request and store operations systems data, such as performance data from the set-top box devices 316, 324. In an illustrative embodiment, the CPE data collection servers may be adapted to analyze performance data to identify a condition of a physical component of a network path associated with a set-top box device, to predict a condition of a physical component of a network path associated with a set-top box device, or any combination thereof.

In an illustrative embodiment, the live acquisition server 354 can transmit content to the AQT switch 352, and the AQT switch 352, in turn, can transmit the content to the OMT switch 360 via the public network 312. In this embodiment, the OMT switch 360 can transmit the content to the TV2 server 362 for display to users accessing the user interface at the TV2 server 362. For example, a user can access the TV2 server 362 using a personal computer 368 coupled to the public network 312.

The avatar engine 130 of FIG. 1 can be operably coupled to the third communication system 300 for purposes similar to those described above.

It should be apparent to one of ordinary skill in the art from the foregoing media communication system embodiments that other suitable media communication systems for distributing broadcast media content as well as peer-to-peer exchange of content can be applied to the present disclosure.

Figure 4:
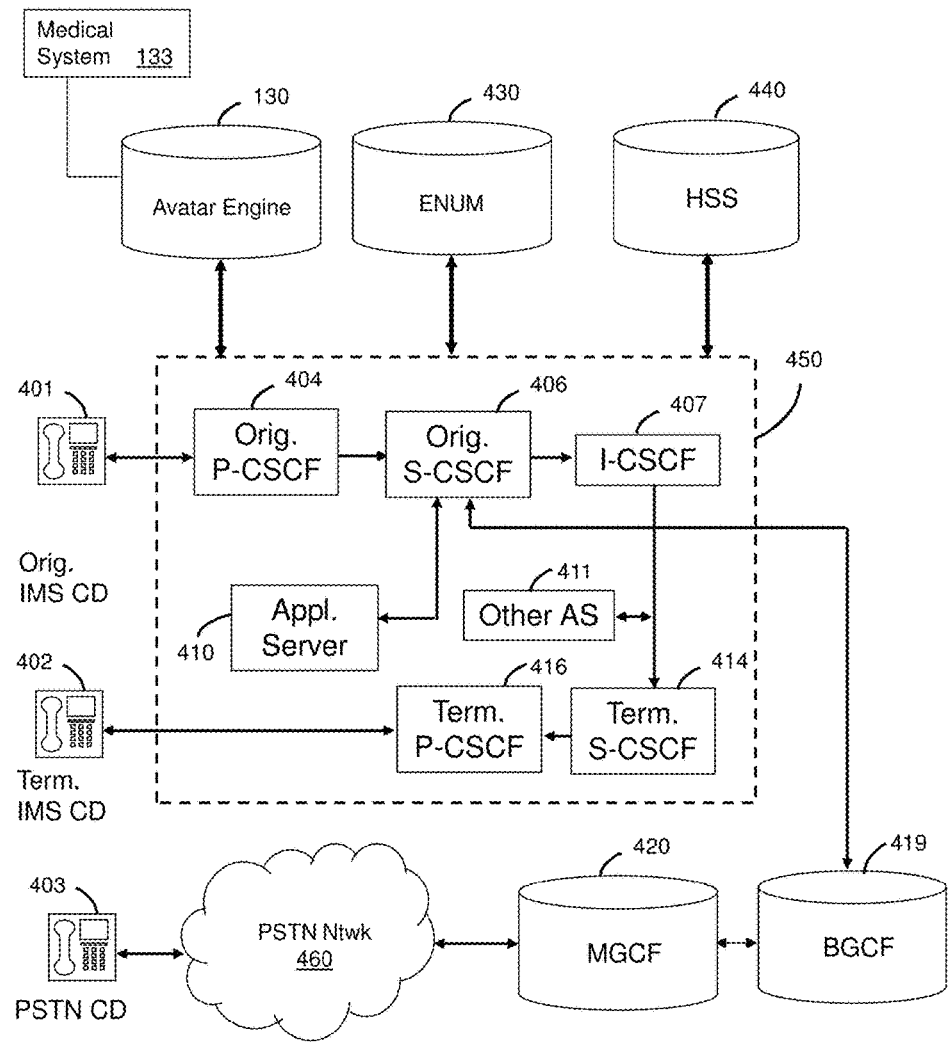

FIG. 4 depicts an illustrative embodiment of a communication system 400 employing an IP Multimedia Subsystem (IMS) network architecture. Communication system 400 can be overlaid or operably coupled with communication systems 100-300 as another representative embodiment of said communication systems.

The communication system 400 can comprise a Home Subscriber Server (HSS) 440, a tElephone NUmber Mapping (ENUM) server 430, and network elements of an IMS network 450. The IMS network 450 can be coupled to IMS compliant communication devices (CD) 401, 402 or a Public Switched Telephone Network (PSTN) CD 403 using a Media Gateway Control Function (MGCF) 420 that connects the call through a common PSTN network 460.

IMS CDs 401, 402 register with the IMS network 450 by contacting a Proxy Call Session Control Function (P-CSCF) which communicates with a corresponding Serving CSCF (S-CSCF) to register the CDs with an Authentication, Authorization and Accounting (AAA) supported by the HSS 440. To accomplish a communication session between CDs, an originating IMS CD 401 can submit a Session Initiation Protocol (SIP INVITE) message to an originating P-CSCF 404 which communicates with a corresponding originating S-CSCF 406. The originating S-CSCF 406 can submit the SIP INVITE message to an application server (AS) such as reference 410 that can provide a variety of services to IMS subscribers. For example, the application server 410 can be used to perform originating treatment functions on the calling party number received by the originating S-CSCF 406 in the SIP INVITE message.

Originating treatment functions can include determining whether the calling party number has international calling services, and/or is requesting special telephony features (such as *72 forward calls, *73 cancel call forwarding, *67 for caller ID blocking, and so on). Additionally, the originating S-CSCF 406 can submit queries to the ENUM system 430 to translate an E.164 telephone number to a SIP Uniform Resource Identifier (URI) if the targeted communication device is IMS compliant. If the targeted communication device is a PSTN device, the ENUM system 430 will respond with an unsuccessful address resolution and the S-CSCF 406 will forward the call to the MGCF 420 via a Breakout Gateway Control Function (BGCF) 419.

When the ENUM server 430 returns a SIP URI, the SIP URI is used by an Interrogating CSCF (I-CSCF) 407 to submit a query to the HSS 440 to identify a terminating S-CSCF 414 associated with a terminating IMS CD such as reference 402. Once identified, the I-CSCF 407 can submit the SIP INVITE to the terminating S-CSCF 414 which can call on an application server 411 similar to reference 410 to perform the originating treatment telephony functions described earlier. The terminating S-CSCF 414 can then identify a terminating P-CSCF 416 associated with the terminating CD 402. The P-CSCF 416 then signals the CD 402 to establish communications. The aforementioned process is symmetrical. Accordingly, the terms "originating" and "terminating" in FIG. 4 can be interchanged.

IMS network 450 can also be operably coupled to the avatar engine 130 previously discussed for FIG. 1. In this representative embodiment, the avatar engine 130 can be accessed over a PSTN or VoIP channel of communication system 400 by common techniques such as described above.

Figure 5:
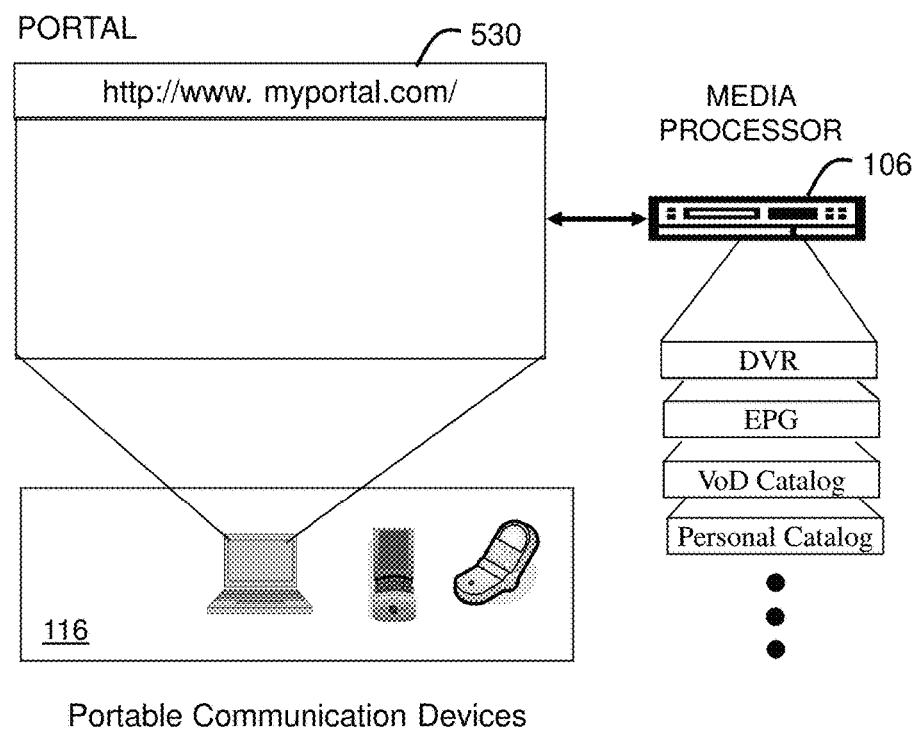
FIG. 5 depicts an illustrative embodiment of a portal interacting with at least one among the communication systems of FIGS. 1-4.

FIG. 5 depicts an illustrative embodiment of a portal 530. The portal 530 can be used for managing services of communication systems 100-400. The portal 530 can be accessed by a Uniform Resource Locator (URL) with a common Internet browser such as Microsoft's Internet Explorer using an Internet-capable communication device such as references 108, 116, or 210 of FIGS. 1-2. The portal 530 can be configured to access a media processor such as references 106, 204, 206, 316, and 324 of FIGS. 1-3 and services managed thereby such as a Digital Video Recorder (DVR), an Electronic Programming Guide (EPG), VoD catalog, a personal catalog (such as personal videos, pictures, audio recordings, etc.) stored in the STB, a personal computer or server in a user's home or office, and so on.

Figure 6:
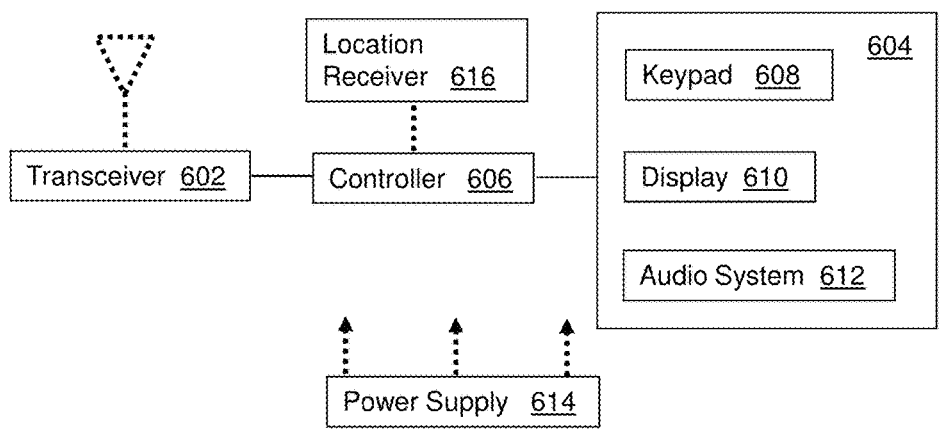
FIG. 6 depicts an illustrative embodiment of a communication device utilized in the communication systems of FIGS. 1-4.

FIG. 6 depicts an exemplary embodiment of a communication device 600. Communication device 600 can be a representative portion of any of the aforementioned communication devices of FIGS. 1-4. The communication device 604 can comprise a wireline and/or wireless transceiver 602 (herein transceiver 602), a user interface (UI) 604, a power supply 614, and a controller 606 for managing operations thereof. The transceiver 602 can support short-range or long-range wireless access technologies such as a Bluetooth wireless access protocol, a Wireless Fidelity (WiFi) access protocol, a Digital Enhanced Cordless Telecommunications (DECT) wireless access protocol, cellular, software defined radio (SDR) and/or WiMAX technologies, just to mention a few. Cellular technologies can include, for example, CDMA-1x, UMTS/HSDPA, GSM/GPRS, TDMA/EDGE, EV/DO, and next generation technologies as they arise.

The transceiver 602 can also support common wireline access technologies such as circuit-switched wireline access technologies, packet-switched wireline access technologies, or combinations thereof. PSTN can represent one of the common circuit-switched wireline access technologies. Voice over Internet Protocol (VoIP), and IP data communications can represent some of the commonly available packet-switched wireline access technologies. The transceiver 602 can also be adapted to support IP Multimedia Subsystem (IMS) protocol for interfacing to an IMS network that can combine PSTN and VoIP communication technologies.

The UI 604 can include a depressible or touch-sensitive keypad 608 and a navigation mechanism such as a roller ball, joystick, mouse, and/or navigation disk for manipulating operations of the communication device 600. The keypad 608 can be an integral part of a housing assembly of the communication device 600 or an independent device operably coupled thereto by a tethered wiring interface (such as a USB) or a wireless interface supporting for example Bluetooth. The keypad 608 can represent a numeric dialing keypad commonly used by phones, and/or a Qwerty keypad with alphanumeric keys.

The UI 604 can further include a display 610 such as monochrome or color LCD (Liquid Crystal Display), OLED (Organic Light Emitting Diode) or other suitable display technology for conveying images to the end user of the communication device 600. In an embodiment where the display 610 is touch-sensitive, a portion or all of the keypad 608 can be presented by way of the display. The UI 604 can also include an audio system 612 that utilizes common audio technology for conveying low volume audio (such as audio heard only in the proximity of a human ear) and high volume audio (such as speakerphone for hands free operation). The audio system 612 can further include a microphone for receiving audible signals of an end user.

The power supply 614 can utilize common power management technologies such as replaceable and rechargeable batteries, supply regulation technologies, and charging system technologies for supplying energy to the components of the communication device 600 to facilitate long-range or short-range portable applications. The controller 606 can utilize computing technologies such as a microprocessor and/or digital signal processor (DSP) with associated storage memory such a Flash, ROM, RAM, SRAM, DRAM or other storage technologies.

Figure 7:
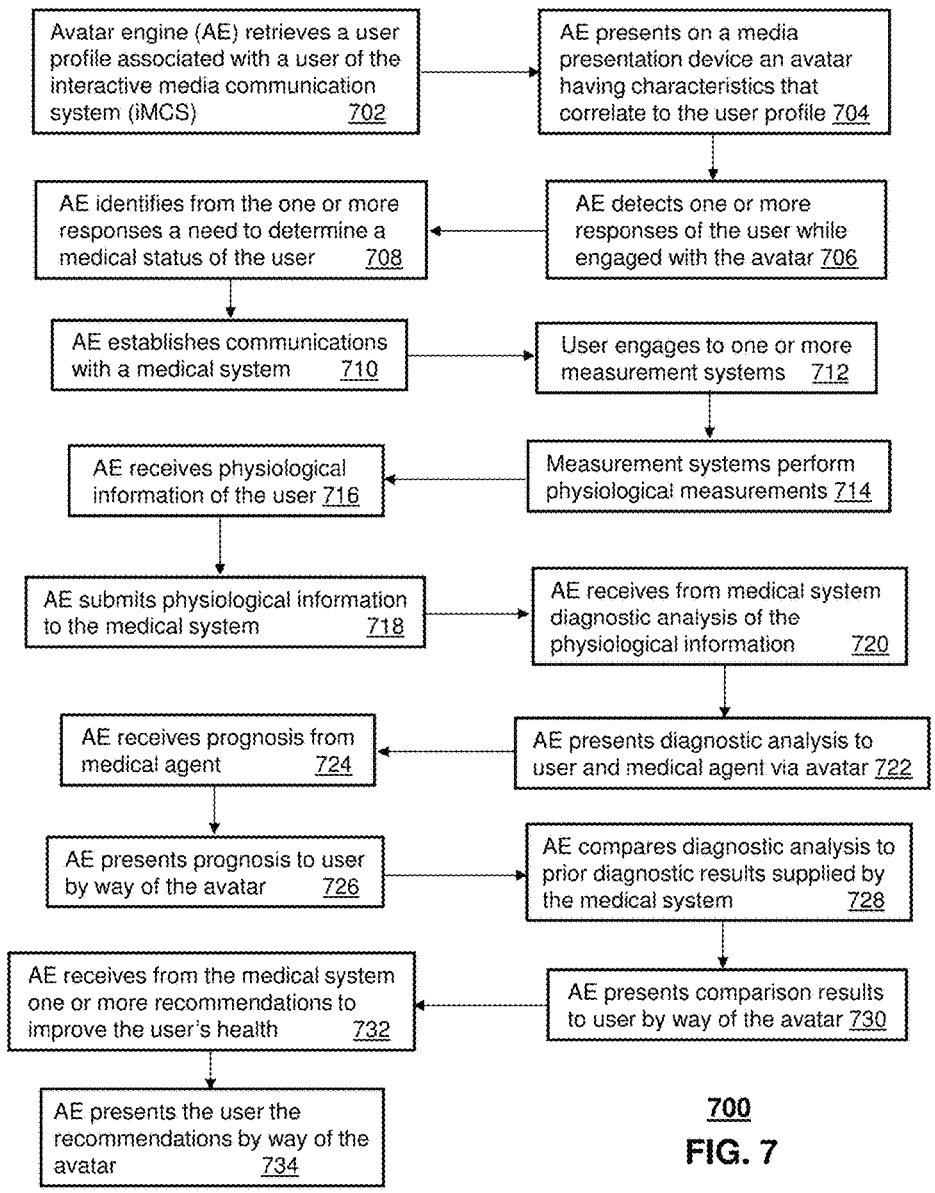
FIG. 7 depicts an illustrative embodiment of a method operating in portions of the communication systems of FIGS. 1-4.
Figure 8:
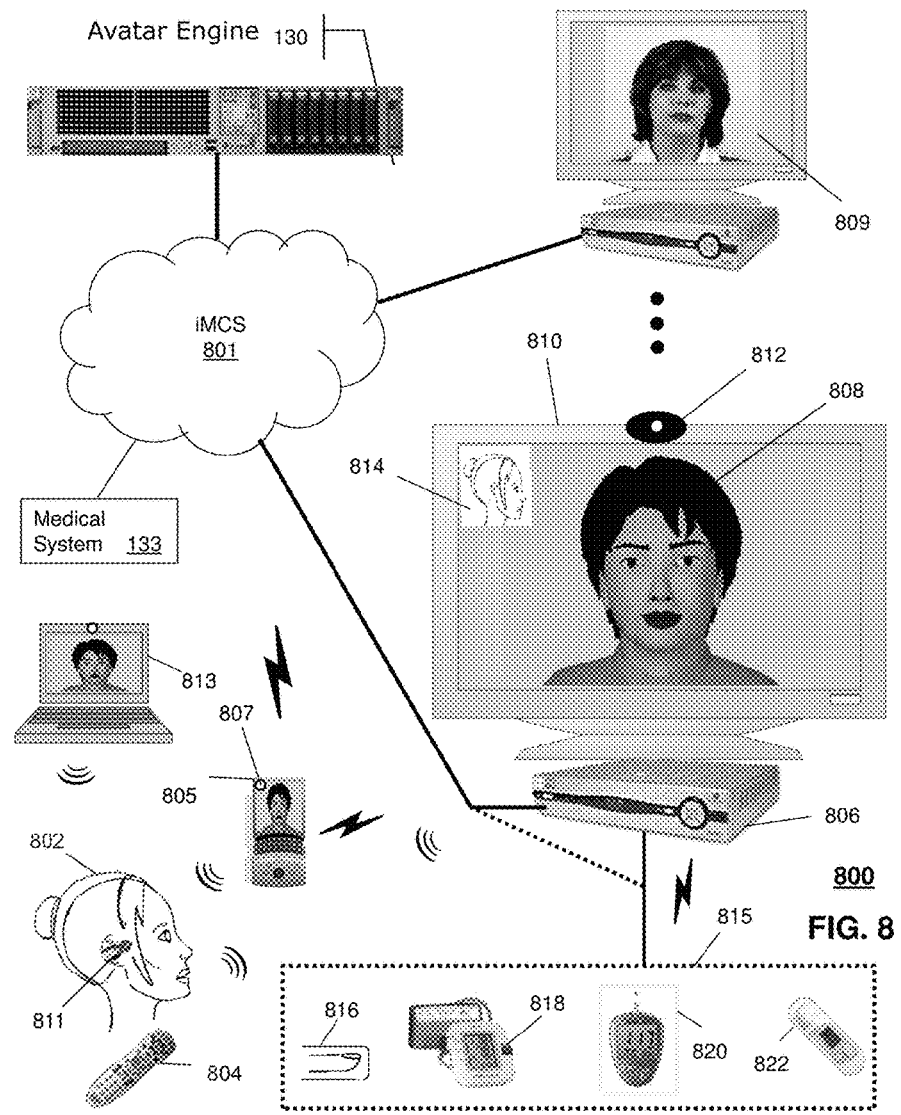
FIG. 8 depicts an illustrative embodiment of a system operating according to the method of FIG. 7.

FIG. 7 depicts an illustrative method 700 operating in portions of communication systems 100-400. FIG. 8 depicts an illustrative embodiment of a system 800 operating according to the method of FIG. 7. FIG. 8 depicts an interactive media communication system 801 such as the systems shown in FIGS. 1-4 (singly or collectively). The interactive media communication system (iMCS) can be coupled to the avatar engine 130 and one or more STBs 806. The STBs 806 can be operatively coupled to media presentation devices such as a high-definition television (HDTV) 810 which can present avatar images 808 (herein referred to avatar 808) supplied by the avatar engine 130 by way of the STBs. A user 802 of the STB 806 can interact with the avatar 808 by speech as well as tactile controls using a remote control 804.

The HDTV 812 can also have a common camera sensor 812 for capturing still and/or moving images of the user 802, which can be displayed in part by the HDTV as a picture-in-picture (PIP) image 814. The visual images of the user can be conveyed to the STB 806. Speech can be detected by a microphone of an audio system of the remote control 804 or an audio system of the STB 806. The avatar 808 can be an animated image, or can have human-like qualities such as the avatar image 809. The STB 806 can transmit to the avatar engine 130 the visual images as well as speech signals of the user 802 for analysis.

The avatar engine 130 can also be communicatively coupled to a mobile phone 805 with a camera 807 that can convey still or moving images of the user 802 to the avatar engine. The mobile phone 805 can have an audio system for receiving responses of the user 802 and for conveying the user's speech to the avatar engine 130. The audio system can also have a loud speaker to convey to the user 802 synthesized speech of the avatar 808 for hands-free operations. To avoid disturbing others, the mobile phone 805 can also incorporate common Bluetooth wireless transceiver technology to communicate with a common Bluetooth headset 811 worn by the user 802. Similarly, the avatar engine 130 can be communicatively coupled to a computer 813 with similar resources as the mobile phone 805.

The avatar engine 130 can further be communicatively coupled directly or indirectly by way of the STB 806 to physiological measurement equipment 815. The measurement equipment 815 can include a standard interface such as a USB port that enables these devices to be tethered to the STB 806 for conveying measurements to the avatar engine 130. Alternatively, these devices can be wirelessly coupled to the STB 806 with technologies such as Bluetooth or WiFi.

FIG. 8 depicts illustrations of the possible types of measurement equipment 815 that can be used by the user 802 to convey physiological information to the medical system 133 by way of the avatar engine 130. The user 802 can for example utilize a pulse oximeter sensor 816 to measure the user's pulse and oxygen saturation in the user's blood. The user 802 can also utilize a blood pressure meter 818, a glucose meter 820, a thermometer 822, as well as other common physiological measurement devices (not shown) to convey physiological data to the avatar engine 130. The avatar engine 130 can establish communications with the medical system 133 described in FIG. 1 by way of the iMCS 801.

With system 800 in mind, method 700 can begin with step 702 in which the avatar engine 130 retrieves a user profile associated with the user 802 of the iMCS 801. This step can be responsive to the user 802 requesting access to the avatar 808 by initiating a speech command or tactile command (such as selecting an avatar request button on the remote control 804) that is detected by the STB 806, and thereby conveyed to the avatar engine 130. The user profile can include demographic profiling information of the user 802, psychographic profiling information of the user, and/or user preferences supplied by the user. The demographic profiling information of the user 802 can be based on age, gender, income, number of occupants in household, occupation, education, value of residential property, location of residential property, and/or fees paid for services rendered by the iMCS 801—just to name a few possibilities.

The demographic profiling information of the user 802 can be determined from a subscriber account of the user and/or monitored media consumption behavior of the user. One or more network elements of the iMCS 801 can utilize common demographic analysis tools to make these determinations. The psychographic profiling information of the user 802 can also be determined from monitored media consumption behavior of the user and/or subscriber account information. Utilizing common psychographic analysis tools, one or more network elements of the iMCS 801 can generate the psychographic profiling information of the user 802. The psychographic profiling information can identify one or more traits, attitudes, interests, and/or lifestyles of the user 802.

User preferences supplied by the user 802 can identify, for example, a preferred gender for the avatar, a preferred image (could be an image of the user 802, an image of a friend or spouse of the user, celebrity, etc.), a preferred personality for the avatar (mild-mannered avatar), preferred search preferences, preferred content sources, preferred merchants for purchasing or selling goods or services, medical profile of the user, and so on.

In step 704 the avatar engine 130 can present on the HDTV 810 the avatar 808 correlated to the user profile as described above. The avatar engine 130 can use common correlation technology to statistically generate an avatar image that is likely suited for the user 802 according to the aforementioned aspects provided by the user profile. Using common speech synthesis and recognition technology, the avatar engine 130 can interact with the user 802 by way of the avatar 808 to provide interactive media services. The interactive function can be initiated by the user 802 with speech or tactile responses on the remote control 804 which can be detected by the avatar engine 130 in step 706 by way of the STB 806.

User responses can represent any detectable visual or audible response of the user 802 determined from an exchange between the user and the avatar engine 130 by way of the avatar 808. A response for example can represent a command such as, "Show me my weight charts", "Record my blood pressure", "Show me my cholesterol data overlaid by my exercise regimen", "Show me my next doctor's appointment", "Show my potential side effects of taking statins", and so on.

The avatar engine 130 can also be programmed, for example, to identify in step 708 from the user's responses a need to determine a medical status of the user. Suppose the user 802 tells the avatar 808 s/he is not feeling well. In step 708 the avatar 808 can ask the user 802 what s/he is feeling, and recommend that the user engage with one or more of the measurement devices 815 available to the user. The avatar engine 130 can establish communications with the medical system 133 in preparation to analyze physiological data supplied by the user 802 by way of the measurement devices 815. Based on the ailment description given by the user 802 and known health conditions supplied in the medical profile of the user, the avatar engine 130 can request by way of the avatar 808 that the user 802 engage in step 712 with the pulse oximetry sensor 816, the blood pressure sensor 818 and the thermometer 822, and provide a blood sample to the glucose sensor 820. As noted earlier, each of these devices can be coupled to the STB 806 by a tethered interface or a wireless interface such as WiFi or Bluetooth.

Once measurements are taken by these devices in step 714, the results can be conveyed to the avatar engine 130 by way of the STB 806 (or by direct access to the avatar engine over the ISP network 132). Upon receiving the physiological data in step 716, the avatar engine 130 submits it to the medical system 133 for analysis in step 718. As described earlier, the medical system 133 can employ artificial intelligence that can function in part as an expert system specialized in performing diagnostic analysis of physiological data. In step 714, the medical system 133 can retrieve a physiological profile of the user (which can be similar or more comprehensive than the medical profile in the user preferences described earlier). The physiological profile can indicate, for example, that the user is 6 feet tall, weighs 200 lbs, has high blood pressure, and suffers from type 1 diabetes. This information can guide the medical system 133 in diagnosing the physiological data supplied by the avatar engine 130.

For example, the medical system 133 can determine that the user's blood pressure has risen higher than usual, while other physiological readings appear normal. Under these circumstances, the medical system 133 can provide the avatar engine 130 the diagnostic results in step 720, which the avatar engine 130 can present to the user and a medical agent of the user (such as a physician or registered nurse). The user 802 and the medical agent can be presented in step 722 the diagnostic results by way of the avatar 808. The medical agent can be contacted by the avatar engine 130 over the ISP network 132 to a computer terminal of the agent which presents the avatar 808. The medical agent can in turn review the diagnostic analysis and provide the avatar engine 130 by way of an interaction with the avatar 808 a prognosis in step 724 subject to medication prescribed for the user 802 by the agent.

In step 726 the avatar engine 130 can inform the user 802 by way of the avatar 808 of the prescribed medication and the prognosis given by the medical agent. The avatar engine 130 can compare in step 728 the diagnostic analysis of step 720 to prior diagnostic results supplied by the medical system 130 to determine whether the user's health condition has improved or deteriorated. The avatar engine 130 can present the user 802 the comparison results in step 730 by way of the avatar 808. The medical system 133 can also provide the avatar engine 130 in step 732 one or more recommendations to improve the user's health. For example, the medical system 133 can recommend that the user avoid certain foods with high sodium levels which can exacerbate the user's high blood pressure. The avatar engine 130 can present the user 802 these recommendations in step 734 by way of the avatar 808.

Upon reviewing the aforementioned embodiments, it would be evident to an artisan with ordinary skill in the art that said embodiments can be modified, reduced, or enhanced without departing from the scope and spirit of the claims described below. For example, method 700 can be adapted so that the medical system 133 provides the prognosis after recommending over the counter non-prescription medication. The method 700 can also be adapted so that the user 802 can describe his/her ailment to the avatar 808 which medical system 133 can then diagnose according to the descriptions provided.

In another embodiment, the avatar engine 130 can be integrated in any communication device. For example, the avatar engine 130 can be an integral part of the STB 806, a mobile phone, a PDA, a gaming console, a communication device of an IMS system such as shown in FIG. 4, a portal, and so on. Additionally, the avatar engine 130 can be distributed between devices. Similarly, the medical system 133 can be integrated in the avatar engine 130 and/or operate as an independent application in the user's computing or communication devices, which can be accessed by the avatar engine 130. In these embodiments, the user 802 can perform the tasks of method 700 in a portable fashion at any location.

It should be apparent from these illustrations that other suitable modifications can be applied to the present disclosure without departing from the scope of the claims below. Accordingly, the reader is directed to the claims section for a fuller understanding of the breadth and scope of the present disclosure.

Figure 9:
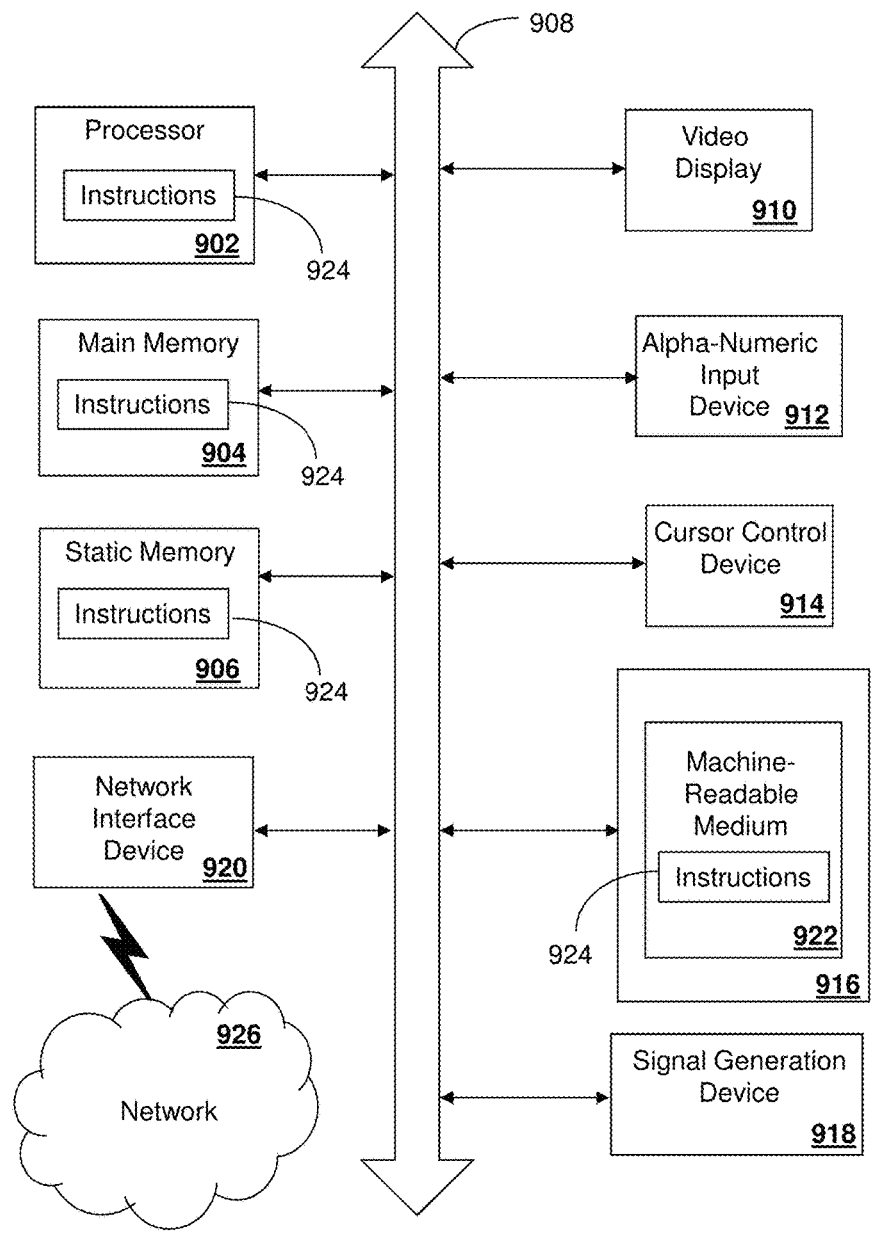
FIG. 9 is a diagrammatic representation of a machine in the form of a computer system within which a set of instructions, when executed, may cause the machine to perform any one or more of the methodologies discussed herein.

FIG. 9 depicts an exemplary diagrammatic representation of a machine in the form of a computer system 900 within which a set of instructions, when executed, may cause the machine to perform any one or more of the methodologies discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

The computer system 900 may include a processor 902 (e.g., a central processing unit (CPU), a graphics processing unit (GPU), or both)), a main memory 904 and a static memory 906, which communicate with each other via a bus 908. The computer system 900 may further include a video display unit 910 (e.g., a liquid crystal display (LCD), a flat panel, a solid state display, or a cathode ray tube (CRT)). The computer system 900 may include an input device 912 (e.g., a keyboard), a cursor control device 914 (e.g., a mouse), a disk drive unit 916, a signal generation device 918 (e.g., a speaker or remote control) and a network interface device 920.

The disk drive unit 916 may include a machine-readable medium 922 on which is stored one or more sets of instructions (e.g., software 924) embodying any one or more of the methodologies or functions described herein, including those methods illustrated above. The instructions 924 may also reside, completely or at least partially, within the main memory 904, the static memory 906, and/or within the processor 902 during execution thereof by the computer system 900. The main memory 904 and the processor 902 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine readable medium containing instructions 924, or that which receives and executes instructions 924 from a propagated signal so that a device connected to a network environment 926 can send or receive voice, video or data, and to communicate over the network 926 using the instructions 924. The instructions 924 may further be transmitted or received over a network 926 via the network interface device 920.

While the machine-readable medium 922 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and/or a digital file attachment to e-mail or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. An avatar engine, comprising:
a processing system including a processor; and
a memory that stores executable instructions that, when executed by the processing system, facilitate performance of operations, comprising:
generating an avatar through equipment of a user, wherein the avatar interacts with the user through the equipment of the user, wherein the equipment of the user provides interactive media services to the user responsive to a command for interactive media service via a plurality of communication exchanges with the avatar;
analyzing an interaction from the plurality of communication exchanges between the avatar and the user to determine whether the interaction indicates a medical need to determine a medical status of the user according to comments received from the user during the interaction;
requesting, by way of the avatar, that the user perform physiological tests to generate current physiological information from the physiological tests responsive to an indication that there is the medical need to determine the medical status of the user;
receiving, by way of a measurement device associated with the equipment of the user, the current physiological information;
accessing prior physiological information of the user;
comparing the prior physiological information with the current physiological information as a comparison;
determining a diagnostic result of the user that indicates an improvement or deterioration in health based on the comparison;
determining whether the diagnostic result requires a prescription-based treatment or a non-prescription treatment;
presenting a recommendation to the user for the non-prescription treatment responsive to an indication that the diagnostic result does not require the prescription-based treatment, wherein the user is presented the diagnostic result by way of the avatar;
presenting the diagnostic result to equipment of a medical agent of the user responsive to an indication that the diagnostic result does require the prescription-based treatment, wherein the medical agent is presented the diagnostic result by way of the avatar;
providing no recommendation to the user responsive to an indication that no prescription or non-prescription treatment is required from the diagnostic result;
receiving from the equipment of the medical agent a prognosis and a prescription determined from the diagnostic result as determined by the medical agent; and
presenting the user with the diagnostic result, the prognosis, and the prescription by way of the avatar.

2. The avatar engine of claim 1, wherein the physiological information comprises one of a body temperature measurement of the user, a blood pressure measurement of the user, a heart rate measurement of the user, a height measurement of the user, a weight measurement of the user, or a body fat measurement of the user.

3. The avatar engine of claim 1, wherein the physiological information is obtained by one of a plurality of selected physiological measuring devices, and
wherein the operations further comprise receiving the physiological information via wireless communication with the one of the plurality of physiological measuring devices.

4. The avatar engine of claim 1, wherein the medical agent corresponds to one of a physician or a nurse, and
wherein the avatar is generated prior to receiving the physiological information, and wherein the avatar engine comprises a set top box providing interactive television services.

5. The avatar engine of claim 1, wherein the operations further comprise presenting to the user by way of the avatar the improvement or deterioration in the diagnostic result of the user, and where the non-prescription treatment comprises a non-prescription medicine.

6. The avatar engine of claim 5, wherein the avatar engine operates in a computing device communicatively coupled to an interactive media communication system comprising an internet protocol television communication system and an internet protocol multimedia subsystem communication system.

7. The avatar engine of claim 1, wherein the operations further comprise presenting an identification of the prescription by way of the avatar.

8. A method, comprising:
generating, by a processing system including a processor, an avatar at equipment of a user, wherein the equipment of the user provides interactive media services to the user via a communication exchange with the avatar;
presenting, by the processing system, the avatar at a device of the equipment of the user;
analyzing, by the processing system, a plurality of communication exchanges between the user and the avatar to determine whether a communication exchange of the plurality of communication exchanges triggers a scenario to initiate an investigation to determine a medical status of the user;
requesting, by the processing system via the avatar, that the user performs physiological tests responsive to the investigation to determine the medical status of the user;
receiving, by the processing system, physiological information from the physiological tests;
determining, by the processing system, whether the physiological information requires a prescription-based treatment or a non-prescription treatment based on an indication of a deterioration of health of the user;

presenting, by the processing system, a recommendation for the non-prescription treatment to the user based on the physiological information responsive to an indication that the deterioration in health of the user indicates a non-prescription based treatment is required;

submitting, by the processing system, the physiological information and the communication exchange to equipment of a medical agent by way of the avatar responsive to an indication that the deterioration in health of the user indicates a prescription-based treatment is required;

providing, by the processing system, no recommendation to the user responsive to an indication that no prescription or non-prescription treatment is required from the deterioration in health of the user;

receiving, by the processing system, from the equipment of the medical agent, a prognosis and a prescription determined from the physiological information and the communication exchange; and presenting, by the processing system, the user with the prognosis and the prescription by way of the avatar.

9. The method of claim 8, wherein the generation of the avatar is based in part on statistical modeling that utilizes a demographic profile of the user and historical media consumption behavior of the user, wherein the avatar is generated prior to receiving the physiological information.

10. The method of claim 8, wherein the medical agent corresponds to one of a physician or a nurse.

11. The method of claim 8, wherein the physiological information comprises one of a body temperature measurement of the user, a blood pressure measurement of the user, a heart rate measurement of the user, a height measurement of the user, a weight measurement of the user, or a body fat measurement of the user.

12. The method of claim 8, wherein the equipment of the medical agent is adapted to retrieve a physiological profile of the user to perform a diagnostic analysis of the physiological information.

13. The method of claim 8, wherein the processing system is communicatively coupled to an interactive media communication system for providing interactive television services.

14. The method of claim 13, wherein the generating the avatar comprises:

retrieving a user profile of a user and an image of the user; and generating an avatar based on the image of the user and based on statistical modeling that utilizes a demographic profile of the user and historical media consumption behavior of the user.

15. A machine-readable storage medium, comprising executable instructions that, when executed by a processing system including a processor, facilitate performance of operations, comprising:

conducting a plurality of communication exchanges between a user and an avatar, wherein interactive media services provided by equipment of the user can be controlled via one of the plurality of communication exchanges based on a command issued by the user;

determining whether a communication exchange of the plurality of communication exchanges triggers a scenario requiring an investigation to determine a medical status of the user;

selecting a physiological measuring device from a group of physiological measuring devices as a selected physiological measuring device responsive to determining the exchange triggers the investigation to determine the medical status of the user;

collecting physiological information associated with the user by the selected physiological measuring device;

accessing prior physiological information associated with the user;

comparing the physiological information associated with the user with the prior physiological information associated with the user to generate a comparison;

determining whether a diagnostic result of the user has changed based on the comparison;

determining whether a change in the diagnostic result indicates a need for a prescription-based treatment or a non-prescription treatment to mediate the change in the diagnostic result;

presenting a recommendation for the non-prescription treatment to the user based on a determination that the change in the diagnostic result indicates a deterioration in health that can be remedied by the non-prescription treatment;

presenting the comparison and a notification that the diagnostic result has changed to equipment of a medical agent of the user by way of the avatar responsive to an indication that the change in the diagnostic result indicates a deterioration in health that can be remedied by the prescription-based treatment;

receiving, from the equipment of the medical agent, one of a prognosis and a prescription as determined by the medical agent from the comparison and a notification that the diagnostic result has changed; and presenting the user with the diagnostic result, the prognosis and the prescription by way of the avatar.

16. The machine-readable storage medium of claim 15, wherein the operations further comprise generating the avatar correlated to a profile of the user.

17. The machine-readable storage medium of claim 15, wherein the selected physiological measuring device comprises a plurality of selected physiological measuring devices from among the group of physiological measuring devices.

18. The machine-readable storage medium of claim 15, wherein the physiological information comprises one of a body temperature measurement of the user, a blood pressure measurement of the user, a heart rate measurement of the user, a height measurement of the user, a weight measurement of the user, a body fat measurement of the user, or any combination thereof.

19. The machine-readable storage medium of claim 15, wherein the avatar is generated prior to receiving the physiological information of the user.

20. The machine-readable storage medium of claim 15, wherein the operations further comprise:

receiving recommendations from the medical agent for healthcare for the user; and presenting the recommendations to the user by way of the avatar.

* * * * *